(12) United States Patent
Carter et al.

(10) Patent No.: US 9,833,173 B2
(45) Date of Patent: Dec. 5, 2017

(54) MATCHING SYSTEM FOR CORRELATING ACCELEROMETER DATA TO KNOWN MOVEMENTS

(71) Applicants: Abraham Carter, Salt Lake City, UT (US); David Scott, North Salt Lake City, UT (US); Maxwell Mann, Falmouth, MA (US)

(72) Inventors: Abraham Carter, Salt Lake City, UT (US); David Scott, North Salt Lake City, UT (US); Maxwell Mann, Falmouth, MA (US)

( * ) Notice: Subject to any disclaimer, the term of this patent is extended or adjusted under 35 U.S.C. 154(b) by 921 days.

(21) Appl. No.: 13/846,662

(22) Filed: Mar. 18, 2013

(65) Prior Publication Data

US 2013/0282324 A1    Oct. 24, 2013

Related U.S. Application Data

(60) Provisional application No. 61/761,626, filed on Feb. 6, 2013, provisional application No. 61/635,827, filed on Apr. 19, 2012.

(51) Int. Cl.
| | |
|---|---|
| *G01P 15/00* | (2006.01) |
| *A61B 5/11* | (2006.01) |
| *A61B 5/00* | (2006.01) |
| *G06F 19/00* | (2011.01) |

(52) U.S. Cl.
CPC .......... *A61B 5/1123* (2013.01); *A61B 5/7257* (2013.01); *A61B 5/7278* (2013.01); *A61B 5/742* (2013.01); *G01P 15/00* (2013.01); *G06F 19/3481* (2013.01)

(58) Field of Classification Search
CPC ...... G01P 15/00; A61B 5/1123; A61B 5/7257
USPC .......................................................... 702/141
See application file for complete search history.

(56) References Cited

U.S. PATENT DOCUMENTS

| | | | |
|---|---|---|---|
| 8,182,424 B2 | 5/2012 | Heckerman | |
| 8,265,900 B2 | 9/2012 | Irlam et al. | |
| 8,317,657 B2 | 11/2012 | Thukral et al. | |
| 2008/0275348 A1* | 11/2008 | Catt | A61B 5/1112 600/483 |
| 2009/0265671 A1 | 10/2009 | Sachs et al. | |
| 2011/0112771 A1 | 5/2011 | French | |
| 2012/0127157 A1 | 5/2012 | Adler et al. | |

(Continued)

OTHER PUBLICATIONS

David Gubbins, "Time Series Analysis and Inverse Theory for Geophysicists", Cambridge University Press, 2004, ISBN, 0521525691, 9780521525695, section 2.3.7.*

(Continued)

*Primary Examiner* — Toan Le
*Assistant Examiner* — Xiuquin Sun
(74) *Attorney, Agent, or Firm* — Michael F. Krieger

(57) ABSTRACT

The present invention extends to methods, systems, and computer program products for providing a matching system for correlating accelerometer data to known movements. Data representing known movements can be obtained and stored in a database such as by processing and storing accelerometer data obtained from one or more accelerometers worn by a user while performing a particular movement. The accelerometer data obtained from a particular movement can be processed to generate a feature set descriptive of the accelerations associated with a particular movement or series of movements.

15 Claims, 9 Drawing Sheets

(56) References Cited

U.S. PATENT DOCUMENTS

| | | |
|---|---|---|
| 2012/0259649 A1 | 10/2012 | Mallon et al. |
| 2012/0277890 A1 | 11/2012 | Han |
| 2012/0289868 A1 | 11/2012 | Chiu et al. |
| 2012/0313847 A1 | 12/2012 | Boda et al. |
| 2012/0316458 A1 | 12/2012 | Rahman et al. |
| 2012/0323496 A1* | 12/2012 | Burroughs ......... G09B 19/0038 702/19 |

OTHER PUBLICATIONS

Emmanueal Munguia Tapia, Using Maching Learning for Real Time Activivty Recognition and Estimation of Energy Expenditure, submitted to the Program in Media Arts and Sciences, School of Architecture and Planning on Mar. 20, 2008. Massachusetts Institute of Technology.

* cited by examiner

MATCHING SYSTEM FOR CORRELATING ACCELEROMETER DATA TO KNOWN MOVEMENTS

CROSS-REFERENCE TO RELATED APPLICATIONS

This application claims priority to U.S. Provisional Patent Application No. 61/761,626 filed Feb. 6, 2013, titled "Matching System For Correlating Accelerometer Data To Known Movements." This application also claims priority to U.S. Provisional Patent Application No. 61/635,827 filed Apr. 19, 2012, titled "Wireless Exercise Tracking."

BACKGROUND

Many devices have been developed for use during exercise to track various parameters of a user's workout. For example, GPS watches can track the total distance traveled by the user, pedometers can count a number of steps a user takes, heart rate monitors can track a user's heart rate, etc.

Although such devices provide beneficial information about the workout, they are unable to distinguish between different types of exercise. For example, a GPS watch, because it only tracks changes in the user's GPS coordinates, cannot determine whether the user is walking, running, biking, or driving in a car. Similarly, a pedometer can detect the occurrence of a step using an accelerometer due to the sudden change in acceleration when the user's foot hits the ground, but cannot determine the specific motion the user's foot is making before hitting the ground.

BRIEF SUMMARY

The present invention extends to methods, systems, and computer program products for providing a matching system for correlating accelerometer data to known movements. Data representing known movements can be obtained and stored in a database such as by processing and storing accelerometer data obtained from one or more accelerometers worn by a user while performing a particular movement. The accelerometer data obtained from a particular movement can be processed to generate a feature set descriptive of the accelerations associated with a particular movement or series of movements.

Once stored, this accelerometer data can be used to analyze current data received from one or more accelerometers worn by a user to identify what movement is currently being performed by the user. In this way, a database of accelerometer data representing virtually any type of movement can be provided.

In some embodiments, the database can be stored on a mobile phone or other mobile device carried by a user during a workout. Accelerometer data being generated by one or more accelerometers worn by the user can be received by the mobile device and compared to the stored accelerometer data in the database to identify the specific movement the user is making during the workout. For example, using the database, it can be determined whether the user is running, biking, doing jumping jacks, bicep curls, push-ups, or virtually any other specific movement. Additionally, accelerometer data representing user defined custom movements can also be obtained and stored.

In one embodiment, the present invention is implemented as a method for identifying a particular movement from accelerometer data by comparing an identified sequence in the accelerometer data to known sequences. A plurality of entries in a database is stored on a portable computing device. Each entry represents one or more known sequences of accelerometer data that are generated when a particular movement is performed. Accelerometer data is received from one or more accelerometers worn by a user while performing a first movement. The database is accessed to determine that the accelerometer data received from the one or more accelerometers includes the one or more known sequences of a first entry. It is then determined that the first entry is associated with a first particular movement.

In another embodiment, the present invention is implemented as a method for creating a custom entry in a database that represents a custom movement performed by a user wearing one or more accelerometers. User input is received that requests that a custom entry be created in a database that stores a plurality of entries. Each entry represents one or more known sequences of accelerometer data that are generated when a particular movement is performed. Accelerometer data is received from one or more accelerometers worn by a user while performing a custom movement. One or more sequences in the accelerometer data that represent the custom movement are identified. The custom entry is then stored in the database. The custom entry includes the one or more identified sequences and an identifier of the custom movement.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
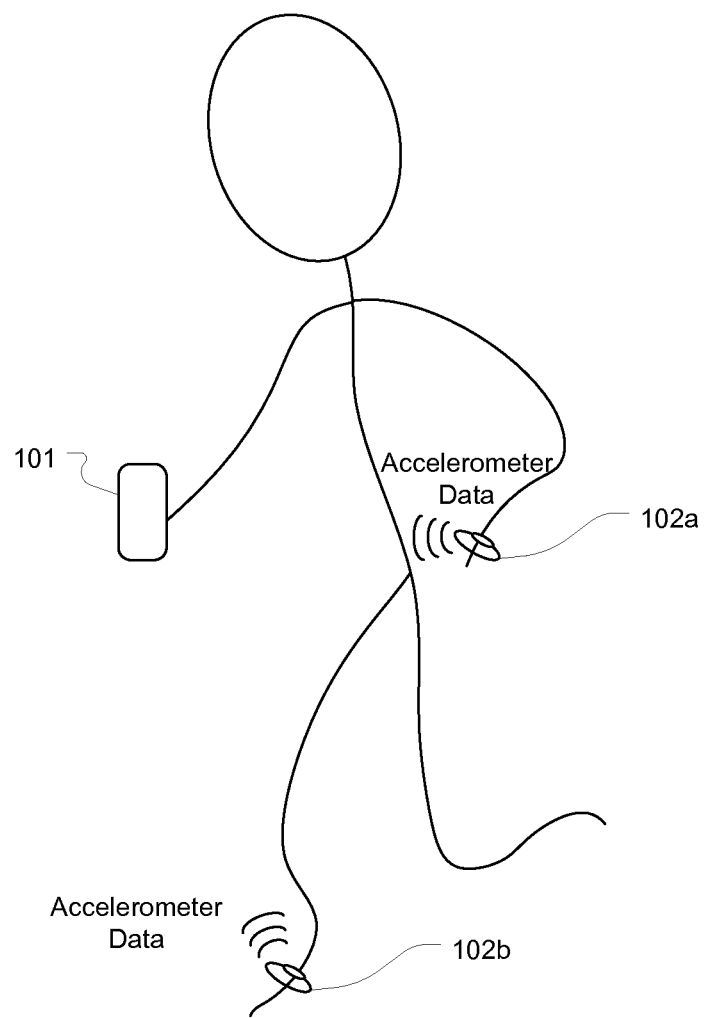
FIG. 1 illustrates an exemplary computing environment in which the present invention can be implemented.

The present invention extends to methods, systems, and computer program products for providing a matching system for correlating accelerometer data to known movements. Data representing known movements can be obtained and stored in a database such as by processing and storing accelerometer data obtained from one or more accelerometers worn by a user while performing a particular movement. The accelerometer data obtained from a particular movement can be processed to generate a feature set descriptive of the accelerations associated with a particular movement or series of movements.

Once stored, this accelerometer data can be used to analyze current data received from one or more accelerometers worn by a user to identify what movement is currently being performed by the user. In this way, a database of accelerometer data representing virtually any type of movement can be provided.

In some embodiments, the database can be stored on a mobile phone or other mobile device carried by a user during a workout. Accelerometer data being generated by one or more accelerometers worn by the user can be received by the mobile device and compared to the stored accelerometer data in the database to identify the specific movement the user is making during the workout. For example, using the database, it can be determined whether the user is running, biking, doing jumping jacks, bicep curls, push-ups, or virtually any other specific movement. Additionally, accelerometer data representing user defined custom movements can also be obtained and stored.

In one embodiment, the present invention is implemented as a method for identifying a particular movement from accelerometer data by comparing an identified sequence in the accelerometer data to known sequences. A plurality of entries in a database is stored on a portable computing device. Each entry represents one or more known sequences of accelerometer data that are generated when a particular movement is performed. Accelerometer data is received from one or more accelerometers worn by a user while performing a first movement. The database is accessed to determine that the accelerometer data received from the one or more accelerometers includes the one or more known sequences of a first entry. It is then determined that the first entry is associated with a first particular movement.

In another embodiment, the present invention is implemented as a method for creating a custom entry in a database that represents a custom movement performed by a user wearing one or more accelerometers. User input is received that requests that a custom entry be created in a database that stores a plurality of entries. Each entry represents one or more known sequences of accelerometer data that are generated when a particular movement is performed. Accelerometer data is received from one or more accelerometers worn by a user while performing a custom movement. One or more sequences in the accelerometer data that represent the custom movement are identified. The custom entry is then stored in the database. The custom entry includes the one or more identified sequences and an identifier of the custom movement.

Embodiments of the present invention may comprise or utilize special purpose or general-purpose computers including computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system.

Computer-readable media is categorized into two disjoint categories: computer storage media and transmission media. Computer storage media (devices) include RAM, ROM, EEPROM, CD-ROM, solid state drives ("SDDs") (e.g., based on RAM), Flash memory, phase-change memory ("PCM"), other types of memory, other optical disk storage, magnetic disk storage or other magnetic storage devices, or any other similarly storage medium which can be used to store desired program code means in the form of computer-executable instructions or data structures and which can be accessed by a general purpose or special purpose computer. Transmission media include signals and carrier waves.

Computer-executable instructions comprise, for example, instructions and data which, when executed by a processor, cause a general purpose computer, special purpose computer, or special purpose processing device to perform a certain function or group of functions. The computer executable instructions may be, for example, binaries, intermediate format instructions such as assembly language or P-Code, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like.

The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices. An example of a distributed system environment is a cloud of networked servers or server resources. Accordingly, the present invention can be hosted in a cloud environment.

FIG. 1 illustrates an exemplary computer environment 100 in which the present invention can be implemented. Computer environment 100 includes a portable computing device 101 and accelerometers 102a, 102b that are worn by a user during a workout or other activity. In a typical implementation, portable computing device 101 can be a user's smart phone or other device capable of running a mobile application (e.g. an MP3 player or tablet). Although two accelerometers are shown, one or more accelerometers can equally be used in conjunction with the database of the present invention.

Accelerometer 102a is shown as being worn around the user's wrist (e.g. as a bracelet), while accelerometer 102b is shown as being worn on or around the user's ankle or foot (e.g. as an anklet, shoe clip, etc.). However, accelerometers 102a, 102b can be worn at any other position of the user's body. In some cases, the specific location of an accelerometer can be based on which body part is performing the movement that the user desires to be identified (e.g. when performing pushups, accelerometer 102a may be placed elsewhere since the wrist remains substantially stationary).

Figure 2:
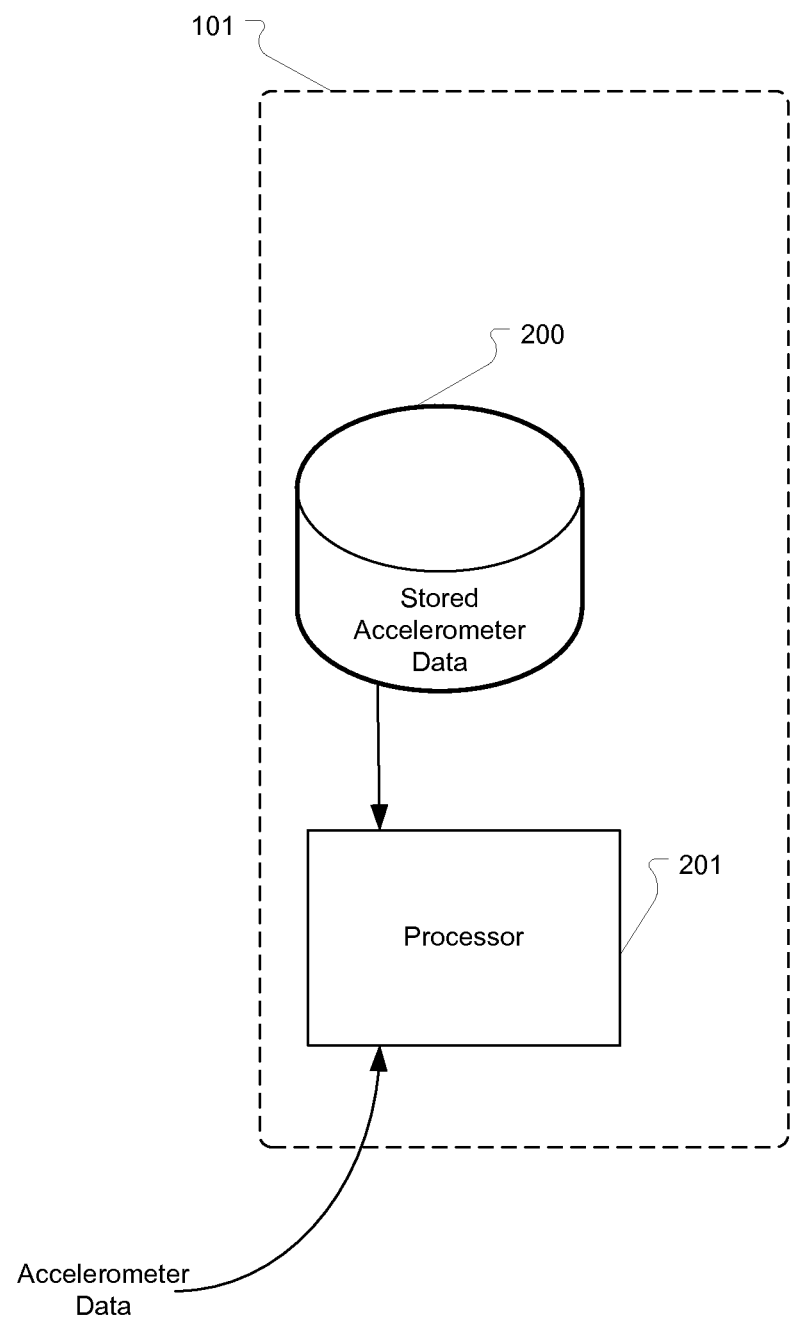
FIGS. 2 illustrates an example configuration of a portable computing device.

FIG. 2 illustrates an example configuration of portable computing device 101. As shown, portable computing device 101 contains a processor 201 and a database 200. Processor 201 is configured to receive accelerometer data from one or more accelerometers (e.g. accelerometers 102a, 102b). Database 200 contains stored accelerometer data representing particular movements. When processor 201 receives accelerometer data from one or more accelerometers, processor 201 can access the stored accelerometer data in database 200 to attempt to match the received accelerometer data to the stored accelerometer data representing a particular movement. If a match is found, processor 201 can store an indication that the user has performed the particular movement.

Figure 3A:
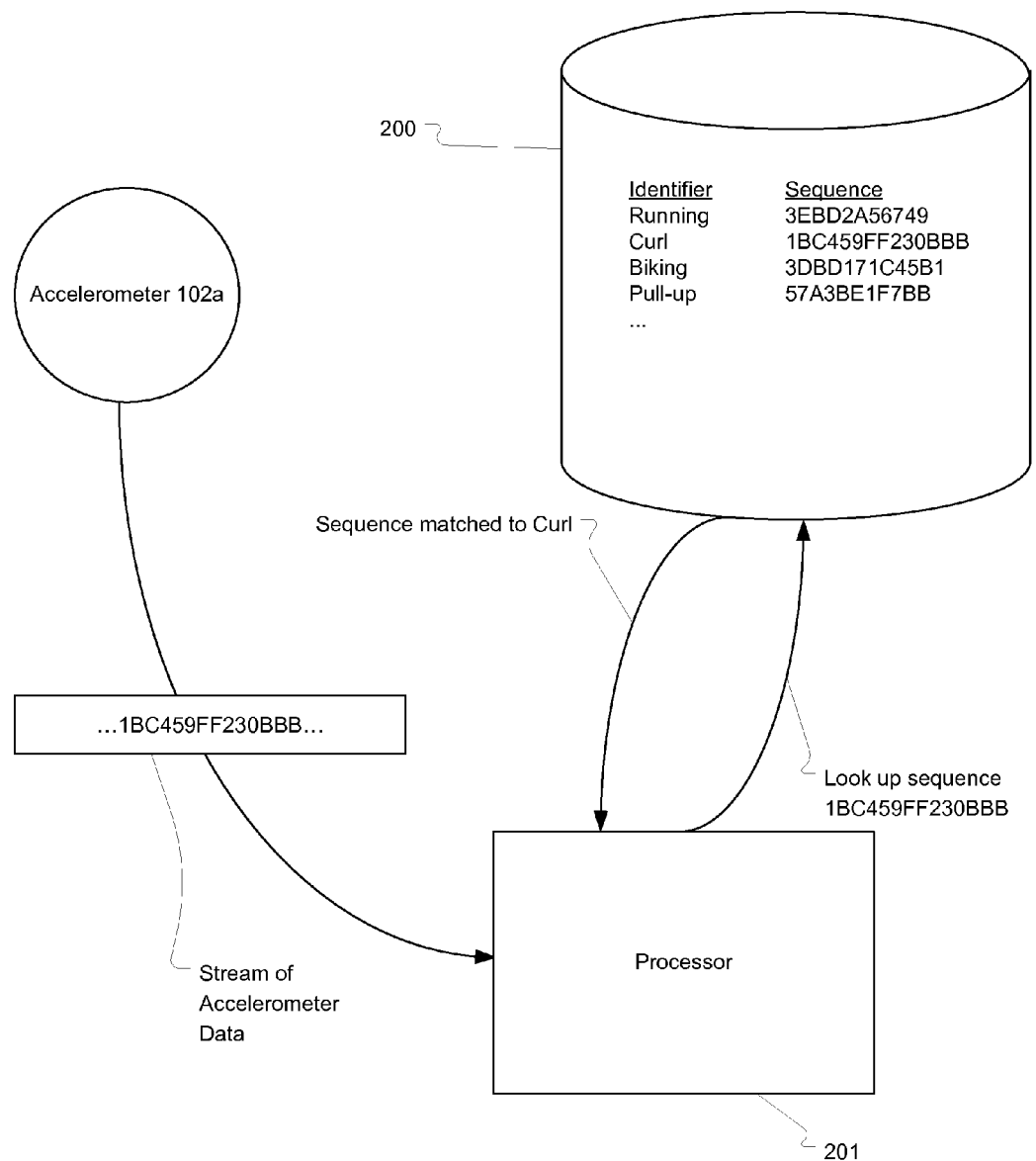
FIGS. 3A and 3B illustrate a simplified example of how this matching can be performed.
Figure 3B:
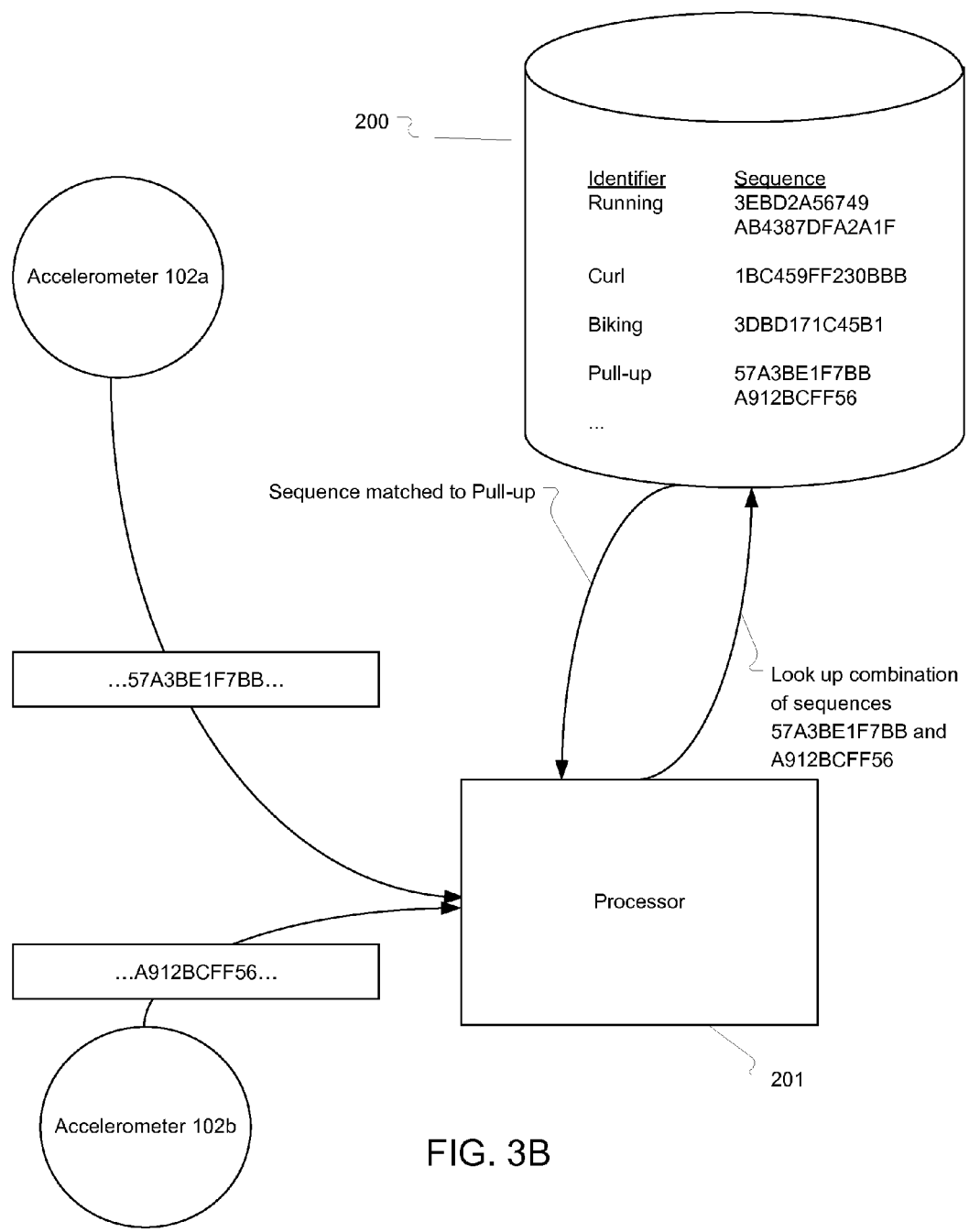

FIGS. 3A and 3B illustrate a simplified example of how this matching can be performed. This simplified example illustrates the direct matching of accelerometer data to known sequences of accelerometer data. However, as further described below, this matching can also be performed by first processing the raw accelerometer data into a more useful format for comparison.

FIG. 3A shows a single accelerometer transmitting a stream of accelerometer data which is received by processor 201. Database 200 is shown as storing various sequences with an associated identifier. Database 200 can be built using known sequences that identify a particular movement. For example, database 200 can be installed on a mobile phone as part of a mobile app.

As mentioned, the depicted sequences in database 200 are simplified to better illustrate the process by which the matching occurs. However, in many cases, rather than a single sequence, a range of sequences or even logic that identifies whether a received sequence matches a particular movement can be used. One specific example of how the data can be stored in database 200 is provided below with respect to FIGS. 5-7.

When processor 201 receives or identifies a sequence in the accelerometer data from accelerometer 102a (which in this example is 1BC459FF230BBB), processor 201 can perform a look-up to identify whether the received sequence matches any stored sequence in database 200. Because the received sequence matches the stored sequence corresponding to Curl, processor 201 can know that the user has performed a curl. Once it is determined that the user has performed a curl, processor 201 can perform various actions such as updating a count of the number of curls performed, updating a display, generating a notification, etc.

FIG. 3B is similar to FIG. 3A but represents in simplified form how a particular movement can be determined using accelerometer data from multiple accelerometers. As shown, both accelerometers 102a and 102b are transmitting accelerometer data representing the movement of the user's body on which each accelerometer is placed.

As in FIG. 3A, processor 201 receives the accelerometer data and performs a look-up. In contrast to FIG. 3A, database 200 is shown as storing two sequences for some movements. For example, the entry for Running includes two sequences which represent the typical motion of an accelerometer attached to the user's shoe and of an accelerometer attached to the user's wrist. The entry for Pull-up likewise includes two sequences.

It is noted that, although only two sequences are shown, it is possible to use more than two sequences for some movements (e.g. when an exercise involves distinct movement of more than two body parts). Also, for some exercises, accelerometer data from only one accelerometer may be required to identify the exercise even if the user is wearing multiple accelerometers. For example, because the user's foot generally remains stationary during a curl (and because it may not be necessary or desirable to identify leg movement during a curl), only one sequence may be stored that represents accelerometer data from an accelerometer on the user's wrist, hand, or arm.

Whether processor 201 receives data from one, two, or more accelerometers, processor 201 can perform a look-up using any or all of the received data. In FIG. 3B, the look-up is performed using sequences 57A3BE1F7BB and A912BCFF56 which match the stored sequences for a pull-up. Accordingly, processor 201 knows that the user has performed a pull-up and can respond accordingly. In another example, if the received accelerometer data had included sequences of 3DBD171C45B1 and 1276BBB34, the look-up could have matched only one of the sequences (the first sequence) which would have identified that the user is pedaling a bike.

In some embodiments, the particular movements identified in database 200 can be highly granular. For example, database 200 can include an entry identifying Running and an entry identifying Running While Pushing A Jogging Stroller. In this example, the entries may contain the same or similar sequence representing the motion of the user's leg while running (e.g. identifying a step), and a sequence representing the motion of the user's arm in each case (e.g. swinging in the case of Running, and stationary in the case of Running While Pushing A Jogging Stroller). Similar distinctions can be made with other types of exercises (e.g. a standard pull-up versus a cross-fit type swinging pull-up).

Figure 4:
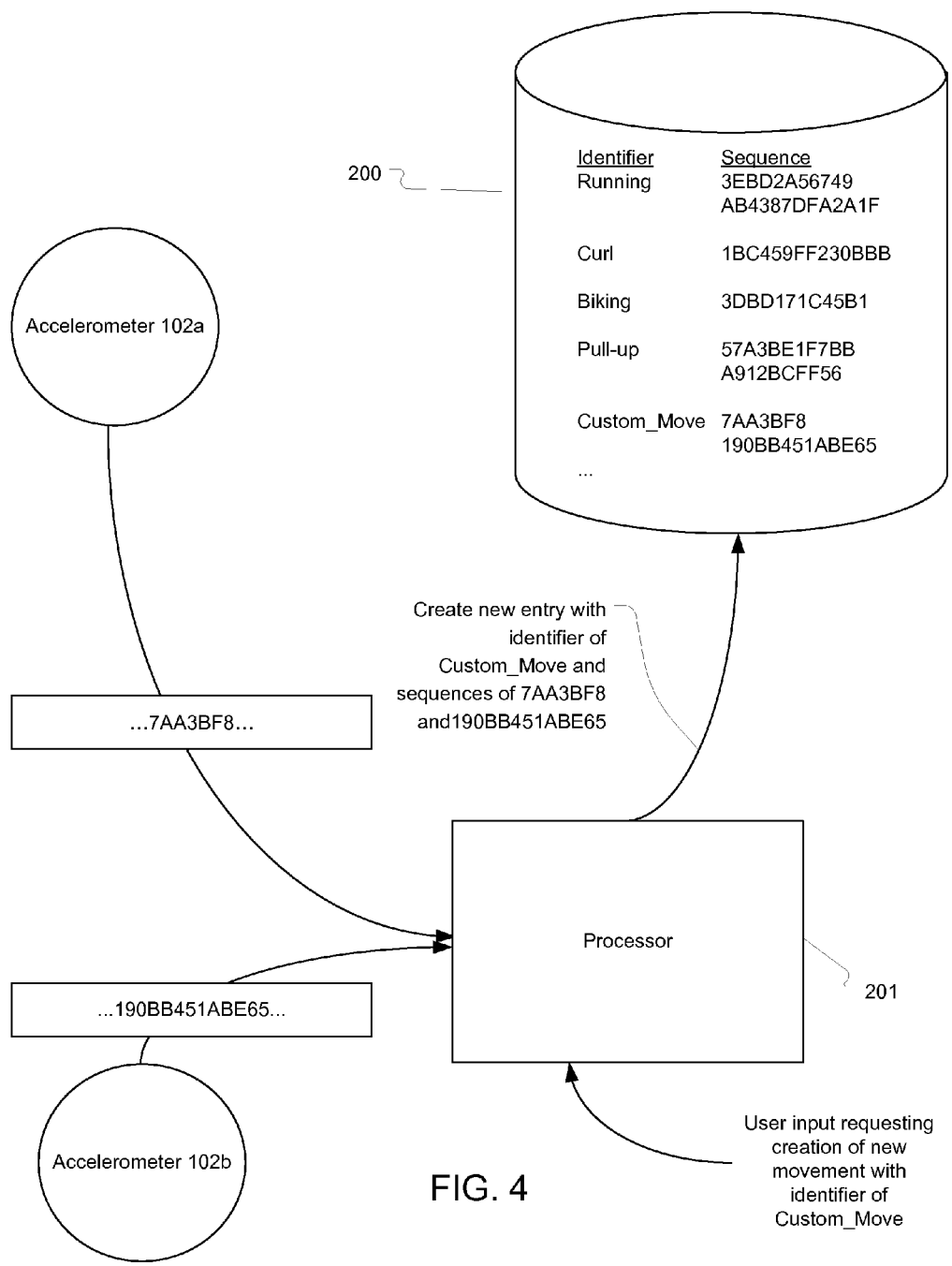
FIG. 4 represents a simplified example of how a user can create a custom entry in a database representing a new or modified movement.

FIG. 4 represents a simplified example of how a user can create a custom entry in database 200 representing a new or modified movement. For example, if database 200 does not include an entry for a particular yoga movement, the user can provide input to processor 201 requesting that a custom entry be created. This can be done by identifying the accelerometer data received from one or more accelerometers while the custom movement is being performed, identifying a sequence within the accelerometer data, and storing the sequence in database 200 with an associated identifier (which may be provided by the user).

FIG. 4 shows that sequences received from both accelerometers 102a and 102b (7AA3BF8 and 190BB451ABE65) are stored in database 200 with an identifier of Custom_Move. Processor 201 can provide various ways for a user to request that a custom move be created. For example, processor 201 can instruct the user to provide input to identify the start and stop of the motion, can provide a time duration during which recording is performed for one iteration of the motion, or can instruct the user to repeatedly perform the movement so that a repeated sequence can be identified in the stream of accelerometer data received. In some embodiments, recording the repeated performance of a custom movement may be preferred because it allows processor 201 to identify variations in accelerometer data during the movement which can allow the creation of a range of sequences or logic for representing the custom movement.

In some embodiments, once a user has created a custom entry in database 200, the custom entry can be shared with other users. For example, if a user has performed a custom cross-fit movement and desires to challenge his friends to perform the same movement, a custom entry created for the movement can be sent to the friends' portable computing devices (either directly or via a central server).

In this manner, database 200 can store entries for virtually any movement. For example, database 200 can initially be supplied with a number of common movements and can later be updated either by receiving user created custom entries or by receiving new entries received from a central server or other users' devices.

Figure 5:
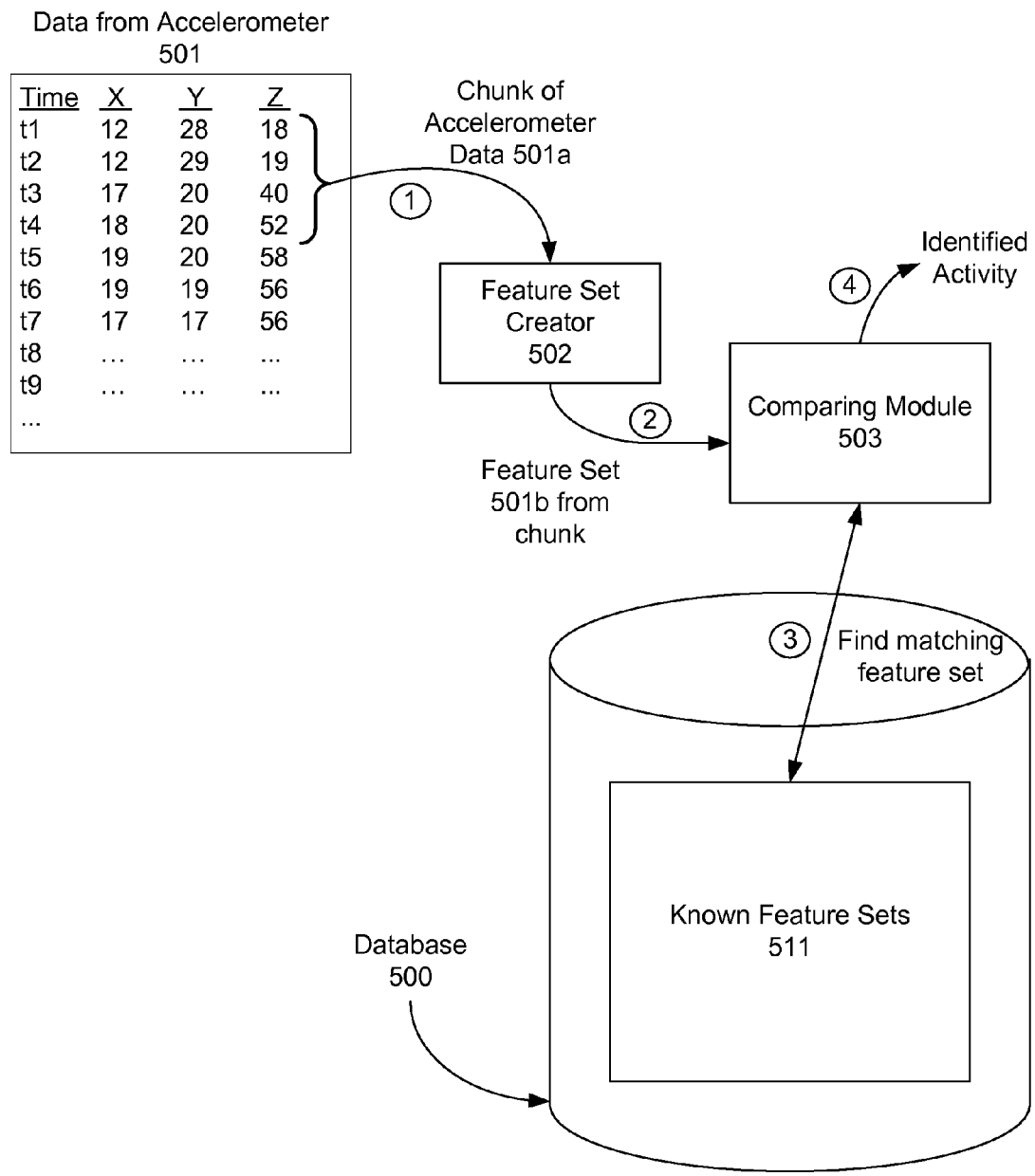
FIG. 5 illustrates a particular example configuration of a portable computing device 101 that can be used to implement the present invention.

FIG. 5 illustrates a particular example configuration of a portable computing device 101 that can be used to implement the present invention. The numbers used to describe accelerometer data in FIGS. 5-8 are exemplary and have been chosen to simplify the description of the invention. However, the specific format used in the described processes can vary as desired.

FIG. 5 shows an example data stream 501 that is received from an accelerometer. In this example, it is assumed that a single accelerometer is being used. However, similar processing can be performed on the data received from one or more other accelerometers.

FIG. 5 represents a general description of the process of converting the data 501 into a feature set that is compared to known feature sets to identify an activity being performed. Data 501 is shown as comprising three axes (x, y, z) of accelerometer readings over a number of time periods (t1-t9).

The first step of the depicted process is to divide data 501 into various chunks. The division of data 501 into chunks can be based on many factors. In the example shown in FIG. 5, a chunk 501a is shown as comprising the accelerometer data received during the time interval t1-t4 (e.g. 4 seconds if a time period is 1 second, 2 seconds if a time period is 0.5 seconds, etc.). The second step comprises feature set creator 502 generating a feature set 501b from chunk 501a. The third step comprises comparing module 503 comparing feature set 501b to the known features sets 511 in database 500 to determine the known feature set that most closely matches feature set 501b. This closest matching feature set represents the activity being performed by the user. Finally, the fourth step comprises outputting the name of this identified activity.

Figure 6:
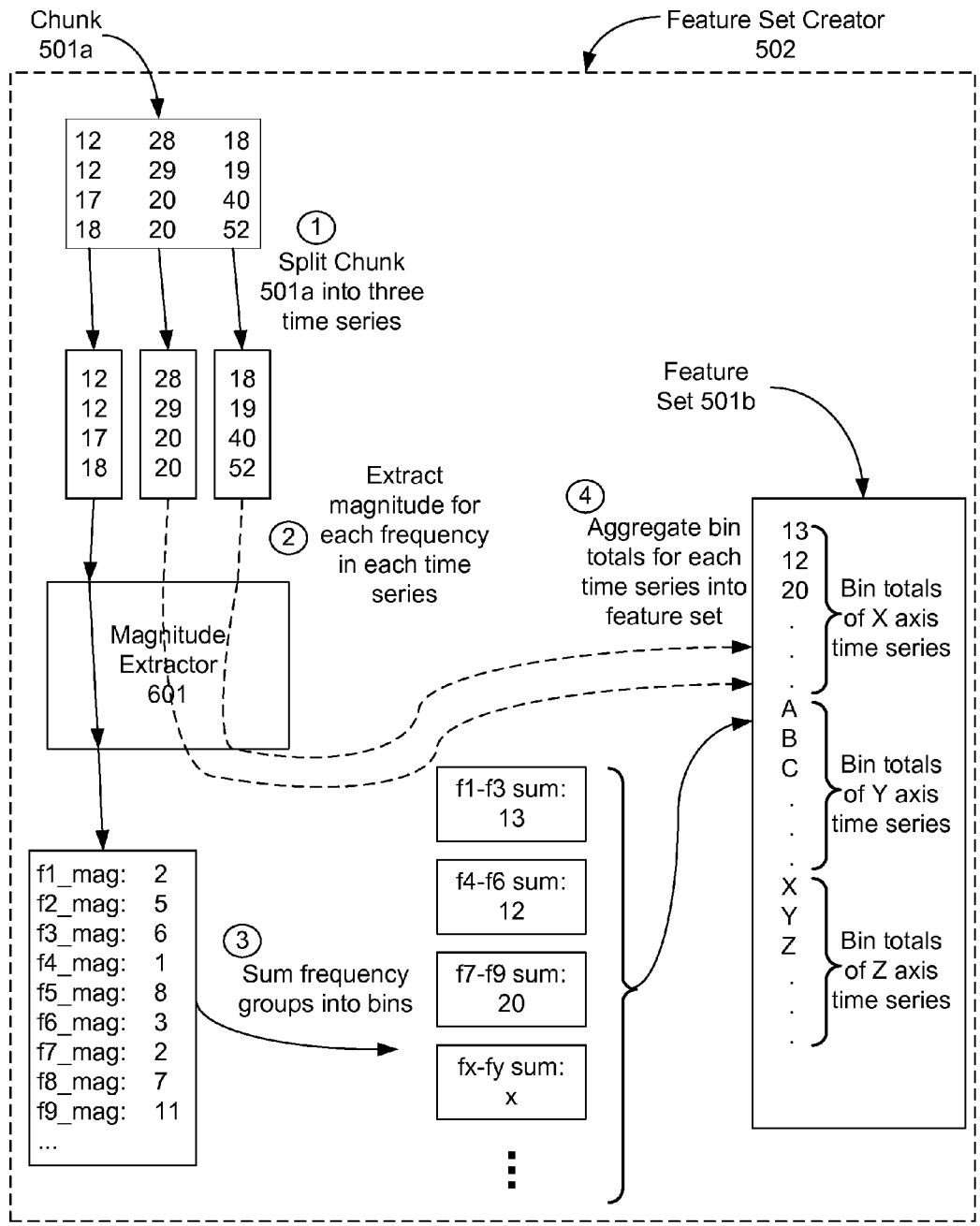
FIG. 6 illustrates how a chunk of accelerometer data is converted into a feature set.

FIG. 6 illustrates a more detailed example of how a chunk is converted into a feature set. As shown, chunk 501a is first split into three time series: one for the x axis data, one for the y axis data, and one for the z axis data in chunk 501a. In In some embodiments, each time series is then further processed independently of the other time series in the chunk. FIG. 6 shows how steps 2 and 3 are applied to the time series for the x axis data while the processing for the y and z axis data is shown simply with dashed lines for clarity. However, in other embodiments, the processing performed on each time series can be interdependent on other times series. Interdependent processing can facilitate consistent scaling of the data to nondimensional speed.

Step 2 involves extracting the magnitude of various frequencies in the data of each time series. In some embodiments, this can be accomplished by applying a Fourier transform to the data, although other techniques could also be used. In FIG. 6, the extracted magnitudes for 9 frequencies (f1_mag-f9_mag) are shown as an example, although other numbers of frequencies could equally be used.

Once the magnitudes of the various frequencies are determined, step 3 involves summing groups of the magnitudes into bins. In FIG. 6, these bins are shown as the sum of the magnitudes of the first through third frequencies, the sum of the fourth through sixth frequencies, the sum of the seventh through ninth, frequencies, etc.

Bins covering different combinations of frequencies can also be used. Also, in some embodiments, no bins (or a bin containing the magnitude of a single frequency) can be used. One benefit of using bins is that the larger the number of frequencies whose magnitudes are summed into a bin, the simpler the processing. However, simplifying the processing by using larger bins reduces the accuracy of the process. Therefore, depending on a particular embodiment, the bin size can be selected to maximize processing efficiency without unreasonably affecting accuracy.

Finally, at step 4, the sums from the bins are aggregated to form feature set 501b. The feature set includes the sums from the bins generated for each time series (i.e. for the y and z time series as well as the x time series) as indicated by the dashed lines from the y and z time series. Accordingly, after this process, feature set 501b is in a format that enables the comparison of accelerometer data to the known feature sets stored in the database.

Figure 7:
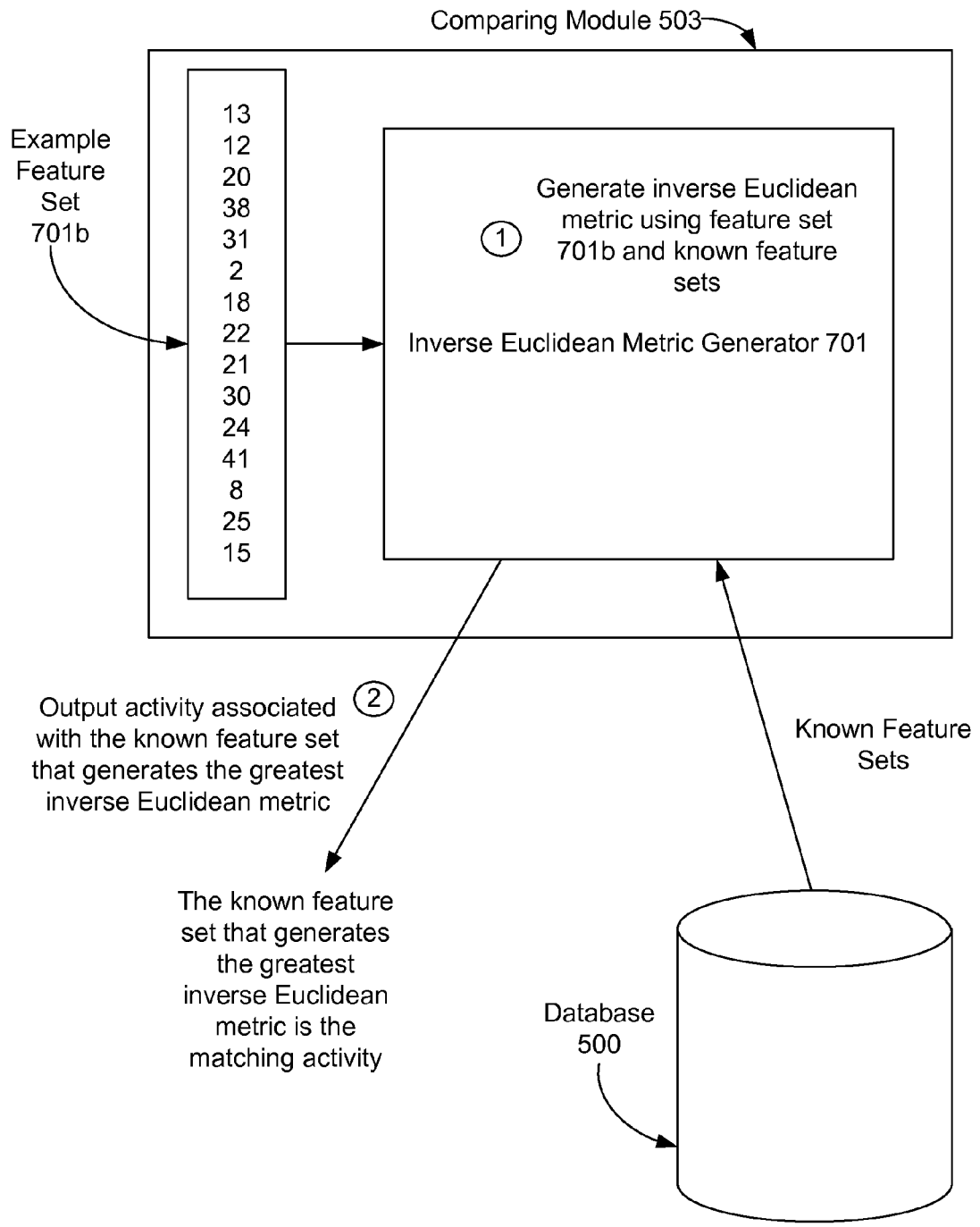
FIG. 7 illustrates how a feature set is compared to known feature sets to identify an activity that is being performed.

FIG. 7 represents an example of how comparing module 503 can compare feature set to the known feature sets to identify an activity being performed. As shown, this comparison can be made using the inverse Euclidean metric of the feature set and each known feature set. The inverse Euclidean metric can be generated from two feature sets using the following function:

$$\frac{1}{\sqrt{\sum_{1}^{i}((featureSet[i]) - (referenceSet[i]))^2}}$$

where i is an index to the bin total, featureSet is the feature set generated from the current received accelerometer data, and referenceSet is the feature set of a known activity. In some embodiments, this function can include a frequency-specific weighting factor such as:

$$\frac{1}{\sqrt{\sum_{1}^{i}((weight[i]) * ((featureSet[i]) - (referenceSet[i]))^2)}}$$

Once the inverse Euclidean metric has been generated for each combination of the feature set and the known feature sets, the inverse Euclidean metric having the greatest value is selected, and the activity associated with the known feature set used to generate the greatest value is output as the matched activity.

Figure 8:
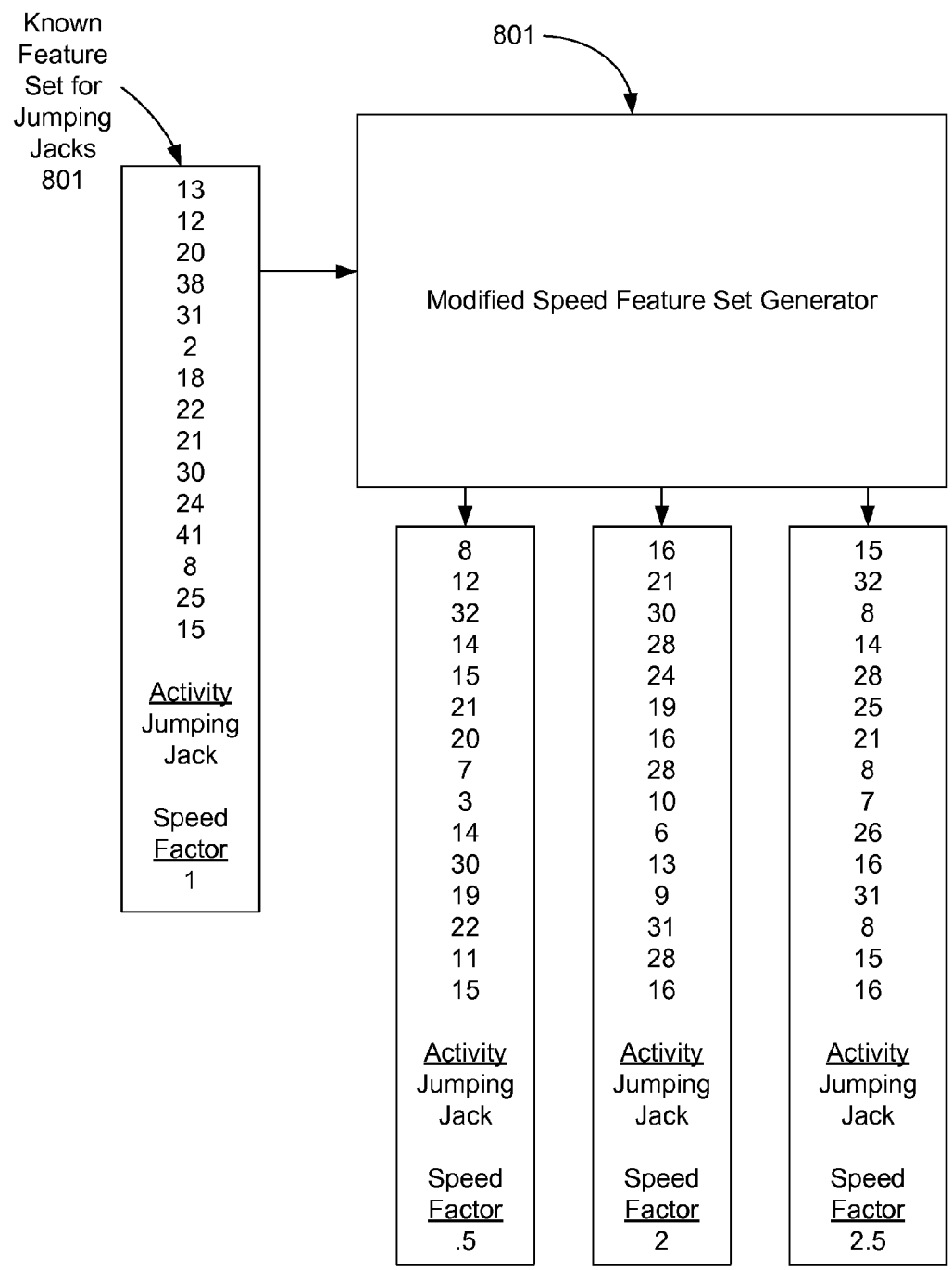
FIG. 8 illustrates how multiple feature sets representing the same activity being performed at different speeds can be generated.

In some embodiments, to ensure that a particular activity can be matched independent of the speed at which the user is performing the particular activity, multiple feature sets can be generated for the particular activity. FIG. 8 illustrates how this can be done. Known feature set 801 represents the feature set generated when jumping jacks are performed at a standard speed. Known feature set includes an indication of the type of activity with which it is associated (i.e. Jumping Jack), and a speed factor which in this case is 1. In other words, the numbers listed in feature set 801 represent the accelerometer data that would be generated when a user is performing jumping jacks at a standard speed.

FIG. 8 includes a modified speed feature set generator 801 which can generate other feature sets from feature set 801. Modified speed feature set generator 801 can generate new feature sets from an existing feature set by modifying the time basis of the input accelerometer data (e.g. by a factor ranging from less than one to greater than one). As shown, three new feature sets have been generated that each represent the jumping jack activity, but correspond to the performance of jumping jacks at a different speed. Specifically, the new feature sets correspond to jumping jacks being performed at half speed, double speed, and two-and-half speed with respect to the reference speed 1 of feature set 801.

In this example, database 200 can store all four feature sets thereby allowing portable computing device 101 to identify not only the specific activity being performed, but the speed at which the activity is being performed. Specifically, because the numbers (i.e. bin totals) in each feature set corresponding to a particular activity will vary (as shown in FIG. 8), the feature set that yields the highest inverse Euclidean metric will be selected as the matching activity. The speed factor (as well as the activity) listed in the matching feature set can be accessed to determine how fast the user is performing the particular activity. In some embodiments, a feature set can also include information regarding the degree of cyclic motion among the frequencies it contains.

Although not shown, when more than one accelerometer is being used, more than one feature set can be used in the comparison step. Using the jumping jack example, accelerometer data from an accelerometer on the user's wrist and from an accelerometer on the user's foot may be required to appropriate detect that a jumping jack (or a specific type of jumping jack) is being performed. In such cases, the process depicted in FIG. 6 can be performed independently on both sets of accelerometer data thereby generating two feature sets. These two features sets can be input to the comparing module 503 which can compare both feature sets to known feature sets.

For example, a known feature set for jumping jacks may actually contain two feature sets (one for the wrist data and one for the foot data). Comparing module 503 can determine whether the input feature sets match both feature sets in the known feature set.

Alternatively, this process of matching multiple feature sets can be performed independently. For example, comparing module 503 can determine which known feature set matches the feature set representing the wrist data, and independently determine which known feature set matches the feature set representing the foot data. Once two match feature sets have been found, a lookup can be performed to determine whether a known activity exists that includes both identified known feature sets (e.g. a known activity for jumping jacks may contain both identified known feature sets). In other words, in this scenario, the movement of the arm is identified separately from the movement of the foot, and then the two identified movements are used to determine whether a known activity exists that includes both movements.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A system implemented by a portable computing device for creating a custom entry in a database that represents a custom movement performed by a user wearing one or more accelerometers, the system comprising:
    wearable devices incorporating accelerometers;
    a portable computing device for receiving wireless input from the wearable devices, said input being formatted into a request that a custom entry be created in a database of the portable computing device that stores a plurality of entries, each custom entry representing one or more feature sets of accelerometer data that are generated when a particular movement is performed;
    the portable computing device receiving accelerometer data from one or more accelerometers worn by a user while performing a custom movement;
    using a processor of the portable computing device to generate one or more feature sets by:
    extracting a chunk of the accelerometer data corresponding to a plurality of axes;
    splitting the chunk into a plurality of time series, each time series including the accelerometer data from a particular axis;
    for each time series, extracting a magnitude of various frequencies in the data of each time series;
    for each time series, summing groups of magnitudes into bins; and
    for each time series, aggregating bins to form feature sets; and
    storing the custom entry in the database, the custom entry including the feature sets and an identifier of the custom movement;
    receiving additional accelerometer data at the portable computing device from the one or more accelerometers worn by the user while performing the custom movement;
    accessing the database with the processor to determine that the additional accelerometer data received from the one or more accelerometers includes the one or more feature sets of the custom entry;
    displaying on the portable computer device an indication that the custom movement has been performed by the user;
    for each of a plurality of feature sets in the database including the feature set of the custom entry, using the processor to determine the inverse Euclidean metric of the feature set of the unknown movement and the feature set; and
    using the processor to determine which feature set of the plurality of feature sets in the database yields the greatest inverse Euclidean metric.

2. The system of claim 1, wherein displaying the indication comprises incrementing a count of the number of times the user has performed the custom movement.

3. The system of claim 1, wherein the custom entry is stored on a first device, the method further comprising:
    transmitting the custom entry to a second device to permit the second device to identify when a second user performs the custom movement.

4. The system of claim 1, wherein the chunk comprises accelerometer data received over a particular interval of time.

5. The system of claim 1, wherein the time series includes accelerometer data from multiple accelerometers.

6. The method of system 1, wherein the chunk is split by the processor into three time series corresponding to each of the x-axis, y-axis, and z-axis and wherein each of the three time series is used by the processor to form the feature sets.

7. A system implemented by a portable computing device for creating a custom entry in a database that represents a custom movement performed by a user wearing one or more accelerometers, the system comprising:
- wearable devices incorporating accelerometers;
- a portable computing device for receiving input from a user requesting that a custom entry be created;
- the portable computing device receiving accelerometer data at the portable computing device from one or more accelerometers worn by the user while performing a custom movement;
- extracting a chunk of the accelerometer data with a processor of the portable computing device;
- splitting the chunk into a time series using the processor;
- extracting a magnitude of at least one frequency in the time series using the processor;
- summing groups of magnitudes into bins using the processor;
- aggregating bins with the processor to form feature sets;
- storing the feature sets as the custom entry that corresponds to the custom movement performed by the user in the database;
- receiving additional accelerometer data at the portable computing device from the one or more accelerometers worn by the user while performing the custom movement;
- accessing the database with the processor to determine that the additional accelerometer data received from the one or more accelerometers includes the one or more feature sets of the custom entry, comprising:
  - for each of a plurality of feature sets in the database including the feature set of the custom entry, using the processor to determine the inverse Euclidean metric of the feature set of the unknown movement and the feature set; and
  - using the processor to determine which feature set of the plurality of feature sets in the database yields the greatest inverse Euclidean metric; and
- displaying an indication that the custom movement associated with the greatest inverse Euclidian metric has been performed by the user.

8. The system of claim 7, wherein the one or more accelerometers comprises a first accelerometer worn around the user's wrist and a second accelerometer worn around the user's ankle.

9. The system of claim 7, wherein the database is located on a portable computing device.

10. The system of claim 7, wherein receiving input from a user requesting that a custom entry be created comprises receiving an identifier of the custom movement from the user.

11. The system of claim 7, wherein receiving input from a user requesting that a custom entry be created comprises receiving an input from the user indicating a start of the custom movement and an input from the user indicating a stop of the custom movement.

12. The system of claim 7, wherein receiving input from a user requesting that a custom entry be created comprises receiving an input from the user indicating a time duration over which the accelerometer data will be received.

13. A method implemented by a portable computing device for creating a custom entry in a database that represents a custom movement performed by a user wearing one or more accelerometers, the method comprising:
- receiving input from a user at the portable computing device requesting that a custom entry be created;
- receiving accelerometer data at the portable computing device from one or more accelerometers worn by the user while performing a custom movement;
- extracting a chunk of the accelerometer data received over a particular time interval using a processor of the portable computing device;
- splitting the chunk into three time series corresponding to each of an x-axis, a y-axis, and a z-axis using the processor;
- extracting a magnitude of various frequencies in the data of each time series using the processor;
- for each time series, summing groups of magnitudes into bins;
- for each time series, aggregating bins to form feature sets;
- storing the feature sets as the custom entry that corresponds to the custom movement performed by the user in a database;
- generating an additional feature set corresponding to the custom movement performed at a different speed;
- receiving additional accelerometer data from the one or more accelerometers worn by the user while performing the custom movement;
- accessing the database to determine that the additional accelerometer data received from the one or more accelerometers includes the one or more feature sets corresponding to the custom movement and to determine the speed at which the custom movement was performed; and
- displaying an indication that the custom movement has been performed by the user and the speed at which the custom movement was performed;
- wherein determining that the additional accelerometer data received from the one or more accelerometers includes the one or more feature sets of the custom movement comprises:
  - for each of a plurality of feature sets in the database including the feature set of the custom entry, determining the inverse Euclidean metric of the feature set of the unknown movement and the feature set; and
  - determining which feature set of the plurality of feature sets in the database yields the greatest inverse Euclidean metric.

14. The method of claim 13, wherein the custom entry further comprises a speed factor.

15. The method of claim 13, wherein the inverse Euclidean metric comprises a frequency-specific weighting factor.

* * * * *